(12) United States Patent
Berndt

(10) Patent No.: US 9,605,294 B2
(45) Date of Patent: Mar. 28, 2017

(54) BACTERIAL PRE-CONCENTRATION AND DETECTION TECHNIQUE

(71) Applicant: Becton, Dickinson and Company, Franklin Lakes, NJ (US)

(72) Inventor: Klaus W. Berndt, Cockeysville, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 14/005,009

(22) PCT Filed: Mar. 7, 2013

(86) PCT No.: PCT/US2013/029592
§ 371 (c)(1),
(2) Date: Sep. 13, 2013

(87) PCT Pub. No.: WO2014/039082
PCT Pub. Date: Mar. 13, 2014

(65) Prior Publication Data
US 2015/0167044 A1 Jun. 18, 2015

Related U.S. Application Data

(60) Provisional application No. 61/696,393, filed on Sep. 4, 2012.

(51) Int. Cl.
*C12M 1/00* (2006.01)
*C12M 3/00* (2006.01)
(Continued)

(52) U.S. Cl.
CPC ............... *C12Q 1/04* (2013.01); *C12Q 1/24* (2013.01); *G01N 2800/26* (2013.01)

(58) Field of Classification Search
CPC ......... C12M 41/36; C12M 41/30; C12Q 1/04; C12Q 1/24; G01N 2800/24
See application file for complete search history.

(56) References Cited

U.S. PATENT DOCUMENTS 3,887,464 A * 6/1975 Ayres ........................... 210/117
4,073,691 A * 2/1978 Ahnell et al. .................. 435/34
(Continued)

FOREIGN PATENT DOCUMENTS

| EP | 2169047 A2 | 3/2010 |
|---|---|---|
| EP | 2430461 A2 | 3/2012 |

(Continued)

OTHER PUBLICATIONS

International Search Report and Written Opinion for Application No. PCT/US2013/029592 dated Jun. 27, 2013.
(Continued)

*Primary Examiner* — Nathan Bowers
(74) *Attorney, Agent, or Firm* — Lerner, David, Littenberg, Krumholz & Mentlik, LLP

(57) ABSTRACT

A bacterial pre-concentration and detection system generally includes a collection tube (110), a sensor (120) at the bottom of the collection tube, a moveable stopper (130) initially located toward the top of the tube, a piston (300) operatively connected to a robot for moving the stopper up or down the inside of the collection tube, and a hollow needle (400) penetrating the stopper and creating fluid communication with the inside of the collection tube. The system allows for the sample to be collected, lysed, centrifuged, concentrated, and interrogated with regard to the presence or absence of microorganisms with minimal steps and with a reduction in the time-to-detection, compared with conventional growth-based bacterial detection systems.

13 Claims, 5 Drawing Sheets

(51) Int. Cl.
*B01L 1/00* (2006.01)
*C12Q 1/04* (2006.01)
*C12Q 1/24* (2006.01)

(56) References Cited

U.S. PATENT DOCUMENTS

| | | | |
|---|---|---|---|
| 4,250,266 A | | 2/1981 | Wade |
| 4,945,060 A | | 7/1990 | Turner et al. |
| 5,047,331 A | * | 9/1991 | Swaine et al. ............... 435/29 |
| 5,518,895 A | * | 5/1996 | Thorpe et al. ............... 435/34 |
| 5,578,269 A | | 11/1996 | Yaremko et al. |
| 5,580,784 A | | 12/1996 | Berndt |
| 5,705,384 A | | 1/1998 | Berndt |
| 5,716,798 A | | 2/1998 | Monthony et al. |
| 5,770,440 A | | 6/1998 | Berndt |
| 5,891,739 A | | 4/1999 | Berndt |
| 6,086,824 A | | 7/2000 | Fanning et al. |
| 6,251,660 B1 | * | 6/2001 | Muir et al. ............... 435/287.2 |
| 6,750,064 B2 | | 6/2004 | Stahly et al. |
| 7,470,371 B2 | * | 12/2008 | Dorian et al. ............... 210/787 |
| 8,633,016 B2 | * | 1/2014 | Parker ............... 435/287.6 |
| 2004/0197771 A1 | | 10/2004 | Powers et al. |
| 2006/0273049 A1 | * | 12/2006 | Leach et al. ............... 210/787 |
| 2006/0281094 A1 | | 12/2006 | Squirrell et al. |
| 2007/0111225 A1 | | 5/2007 | Lambert et al. |
| 2007/0298487 A1 | * | 12/2007 | Bachur et al. ............... 435/287.2 |
| 2008/0072664 A1 | | 3/2008 | Hansen et al. |
| 2010/0120133 A1 | | 5/2010 | Walsh et al. |
| 2010/0255484 A1 | * | 10/2010 | Halverson ............... G01N 1/38 435/6.1 |
| 2010/0291618 A1 | | 11/2010 | Robinson et al. |
| 2011/0100921 A1 | * | 5/2011 | Heinrich ............... A61M 1/1081 210/670 |
| 2012/0009588 A1 | * | 1/2012 | Rajagopal et al. ............... 435/6.15 |
| 2013/0236955 A1 | * | 9/2013 | Huchler ............... C12M 23/58 435/325 |

FOREIGN PATENT DOCUMENTS

| | | |
|---|---|---|
| KR | 10-1999-0022328 | 3/1999 |
| WO | WO-2012065618 A1 * | 5/2012 |

OTHER PUBLICATIONS

B L Wasilauskas et al: "Isolator component responsible for inhibition of Mycobacterium avium-M. intracellulare in BACTEC 12B medium" Journal of Clinical Microbiology, vol. 35, No. 3, Mar. 1, 1997 (Mar. 1, 1997), pp. 588-590, XP055248314, US ISSN: 0095-1137 * abstract *.
Partial supplementary European Search Report for Application No. 13835110.0 dated Feb. 19, 2016.
Chinese Search Report within Chinese Office Action dated Sep. 1, 2016 for Chinese Application No. 201280069701.X.
G. Funke et al., Use of the BD Phoenix Automated Microbiology System for Direct Identification and Susceptibility Testing of Gram-Negative Rods from Positive Blood Cultures in a Three-Phase Trial; Journal of Clinical Microbiology, vol. 42, No. 4, pp. 1466-1470, published Apr. 2004.
C. Estes et al., "Reagentless detection of microorganisms by intrinsic fluorescence", Biosensors and Bioelectronics vol. 18 (2003), pp. 511-519; published May 2003.
Carbonnelle et al. (2007) Rapid identification of Staphylococci isolated in clinical microbiology laboratories by matrix-assisted laser desorption ionization-time of flight mass spectrometry. J Clin Microbiol 45 2156-61.
Anhalt J, Fenselau C (1975) Identification of bacteria using mass spectrometry. Anal Chem 47219-25,.
Degand et al. (2008) Matrix-assisted laser desorption ionization-time of flight mass spectrometry for identification of nonfermenting gram negative bacilli isolated from cystic fibrosis patients. J Clin Microbiol 46: 3361-7.
General information on SST tubes from Becton Dickinson website (2010).
Isenberg et al. Prototype of a Fully Automated Device for Determination of Bacterial Antibiotic Susceptibility in the Clinical Laboratory; Applied Microbiology, vol. 22, No. 6, pp. 980-986, published Dec. 1971.
Wm. M. Dunne, Jr., et al., In-house validation of the BACTEC 9240 blood culture system for detection of bacterial contamination in platelet concentrates; Transfusion, vol. 45, pp. 1138-1142, published Jul. 2005.
M.J. Bruins et al. Identification and Susceptibility Testing of Enterobacteriaceae and Pseudomonas aeruginosa by Direct Inoculation from Positive BACTEC Blood Culture Bottles into Vitek 2; Journal of Clinical Microbiology, vol. 42, No. 1, pp. 7-11, published Jan. 2004.
G. M. Trenholme et al., Clinical Impact of Rapid Identification and Susceptibility Testing of Bacterial Blood Culture Isolates; Journal of Clinical Microbiology, vol. 27, No. 6, pp. 1342-1345; published Jun. 1989.
M. S. Ammor; Recent Advances in the Use of Intrinsic Fluorescence for Bacterial Identification and Characterization; Journal of Fluorescence, vol. 17, pp. 455-459; published Jul. 12, 2007.
Q. Zhu et al., Raman Spectroscopic Measurement of Relative Concentrations in Mixtures of Oral Bacteria; Applied Spectroscopy, vol. 61, No. 11, pp. 1233-1237; published Nov. 2007.
L. Leblanc et al. Monitoring the identity of bacteria using their intrinsic fluorescence; FEMS Microbiology Letters, vol. 211, pp. 147-153: published Apr. 17, 2002.
K. Gopinath et al., Novel Method for Clearing Red Blood Cell Debris From BacT/Alert Blood Culture Medium for Improved Microscopic and Antimycobacterial Drug Susceptibility Test Results; Journal of Clinical Laboratory Analysis, vol. 21, pp. 220-226, published 2007.

* cited by examiner

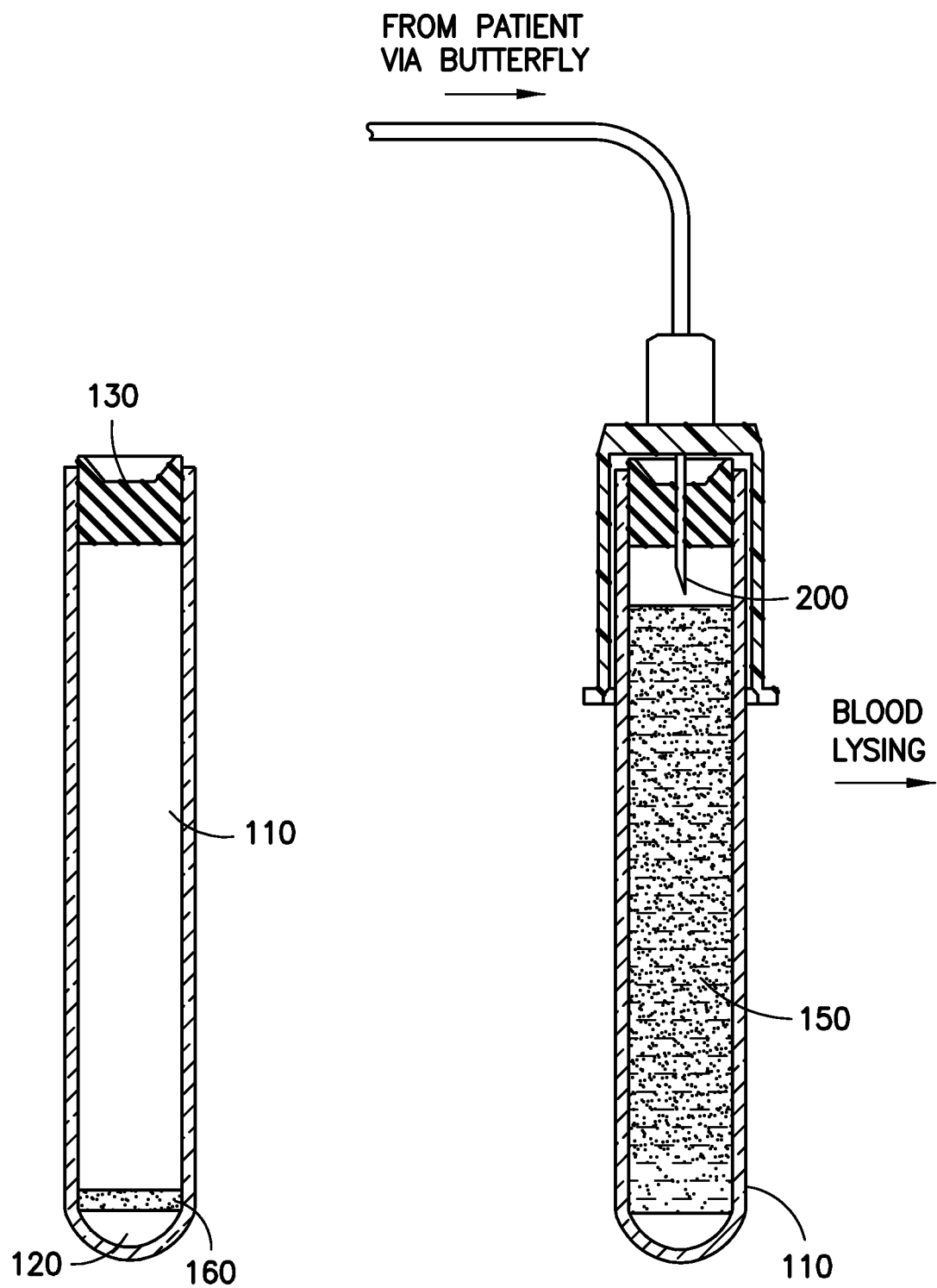

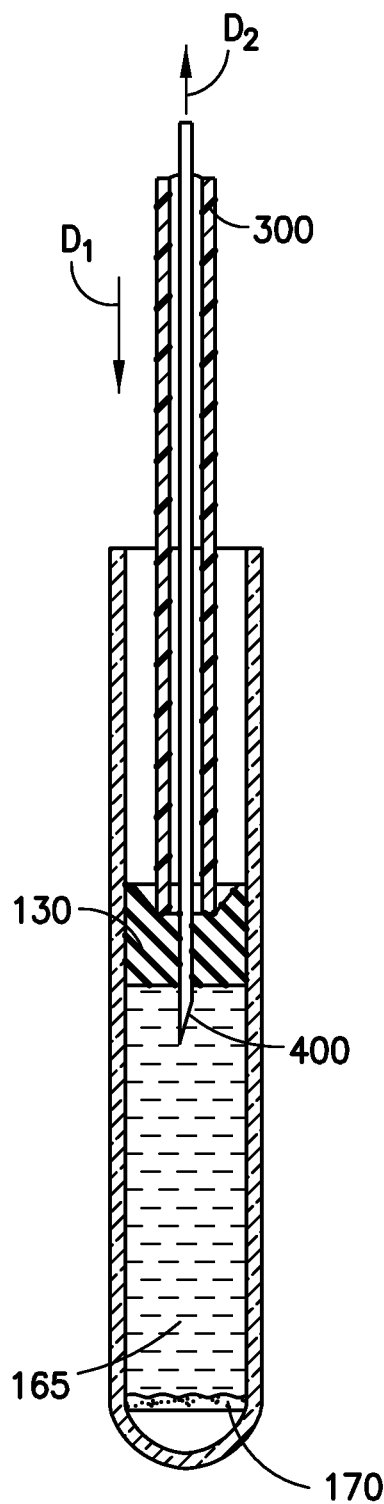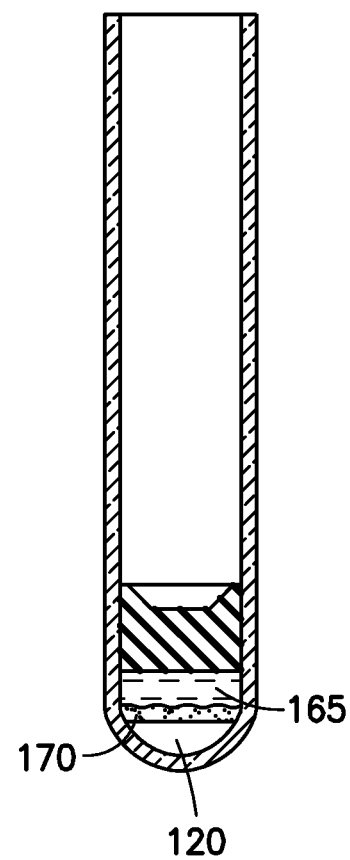
FIG.5
FIG.6

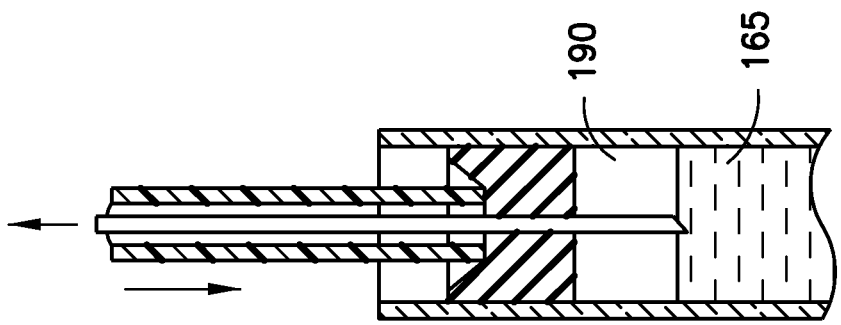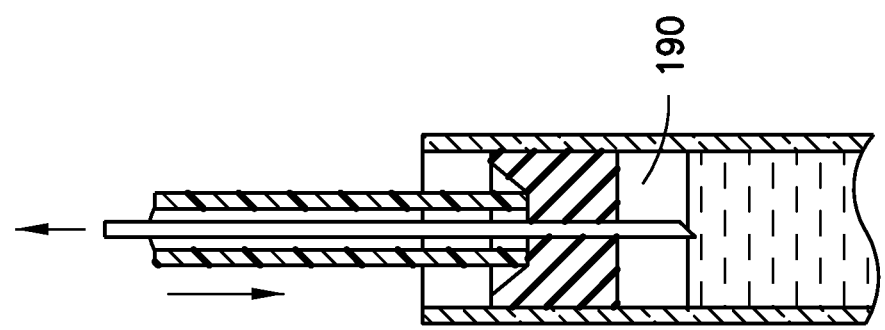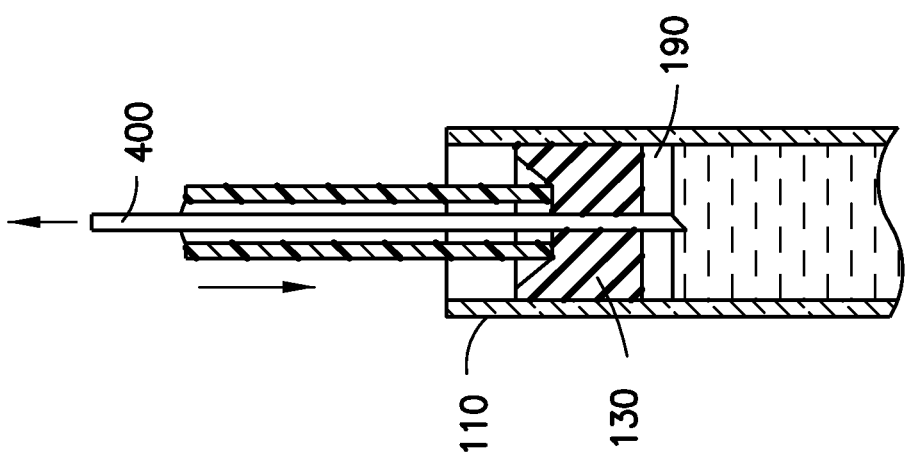

BACTERIAL PRE-CONCENTRATION AND DETECTION TECHNIQUE

CROSS REFERENCE TO RELATED APPLICATIONS

The present application claims the benefit of the filing date of U.S. Provisional Patent Application No. 61/696,393 filed Sep. 4, 2012, the disclosure of which is hereby incorporated herein by reference.

BACKGROUND OF THE INVENTION

Sepsis is a significant healthcare issue due to its high frequency of occurrence and high mortality rate in hospitals. Sepsis is characterized by a whole-body inflammatory state, called a systemic inflammatory response (SIRS), and by the presence of a known or suspected infection. The immune system may cause this inflammatory response as a consequence of microbes in the blood, urine, lungs, skin, or other tissues, for example. One of the leading causes of sepsis is a bloodstream infection (BSI). BSI is most commonly diagnosed by a blood culture, in which a sample of blood is incubated with a medium in an atmosphere controlled to promote bacterial growth. Current automated blood culture systems can take 12-48 hours to detect the presence of infectious microorganisms in blood and can take up to 5 days to rule out the presence of any infectious microorganisms. It can take up to another 12-48 hours to identify the infectious microorganisms by sub-culturing the positive blood culture and performing identification and antimicrobial susceptibility tests. These results can be too late to alter the treatment course and result in the death of the patient. It would be advantageous if the time it takes to detect the presence of infectious microorganisms in the blood or other body fluid or tissue could be shortened to less than 24 hours, and more preferentially to less than 8 hours. Consequently, more time effective methods and apparatus for detecting the presence or absence of infectious microorganisms in a biological sample to determine, for example, if a patient has a BSI continue to be sought.

Bacteria in clinical blood samples are usually detected by inoculating approximately 10 ml of whole blood in a culture bottle, incubating the bottle in an automated system at 35° C., and monitoring products of bacterial metabolism (such as carbon dioxide) by means of sensors disposed within the culture bottle.

The presence of a growing bacterial population within a culture bottle of 90 ml overall volume is typically detected when the number of microorganisms has risen to approximately $5 \times 10^9$. Many bacterial doubling events are required to grow a bacterial population from one or two organisms in the 10 mL blood sample to such a high number. One approach to faster bacterial detection is splitting the 10 ml sample liquid together with the required growth media of typically 40 mL volume into a large number of smaller partial samples that are contained in closed small chambers (see U.S. Pat. Nos. 5,770,440 and 5,891,739 to Berndt, the entire contents of which are both hereby incorporated by reference herein). If the small chambers are not closed, but have a joint head space volume, the shortened Time to Detection (TTD) that is achieved may be less than is desired (see U.S. Pat. No. 5,716,798 to Monthony et al., the entire contents of which are hereby incorporated by reference herein).

While the splitting of the original 10-mL blood sample together with the 40 mL of growth media may achieve faster bacterial detection, the design of a practical multi-chamber sample container remains challenging. Also, if one or two of the small chambers contain sample that shows signs of bacterial growth, there is a need for removal of the sample liquid from those chambers for post-processing procedures such as identification or antibiotic susceptibility testing. Such sample removal represents a further challenge. Also, it is not certain that 10 mL of clinical blood sample is such a small volume that it will contain only one colony forming unit ("CFU"). Such small volumes may very well contain not only two but maybe up to 100 CFUs. In this case, one would waste valuable detection time by distributing the organisms of such bacteria-rich sample into many chambers, whereby each chamber would likely contain either no organism or one organism. For each individual organism, it would take approximately seven doublings to achieve again the number 100. Seven doubling times of approximately two hours for slow growers would mean 14 hours of lost detection time.

In view of this, there exists still a need for a faster bacterial detection technique that neither (i) requires a multi-chamber sample container nor (ii) is prone to wasting valuable detection time in the case of bacteria-rich blood samples.

BRIEF SUMMARY OF THE INVENTION

Described herein are methods and apparatus for pre-concentration and rapid detection of microorganisms in biological samples (e.g. blood) for analysis to determine the presence or absence of infectious microorganisms in the samples. The apparatus includes a collection tube, a mechanism for concentrating the sample in the collection tube and a sensor disposed in the tube at a location that ensures contact between the concentrated sample and the detector.

According to the methods described herein, the sample is collected and concentrated in situ in the collection container using a mechanism to force all but the lowest fraction of the sample from the container to facilitate determining the presence or absence of microorganisms in the sample quickly and without the need to grow large numbers of microorganisms from the sample to facilitate detection.

BRIEF DESCRIPTION OF THE DRAWINGS

FIG. 1 illustrates an evacuated collection tube according to one embodiment of the invention;

FIG. 2 illustrates a blood collection step using the collection tube of FIG. 1;

FIG. 5 illustrates the collection tube of FIG. 4 undergoing a volume reduction step;

FIG. 6 illustrates the collection tube of FIG. 5 after the completion of a volume reduction step;

FIGS. 7A-C illustrate different controlled headspace gas volumes in a collection tube according to one embodiment of the invention.

DETAILED DESCRIPTION

Figure 3:
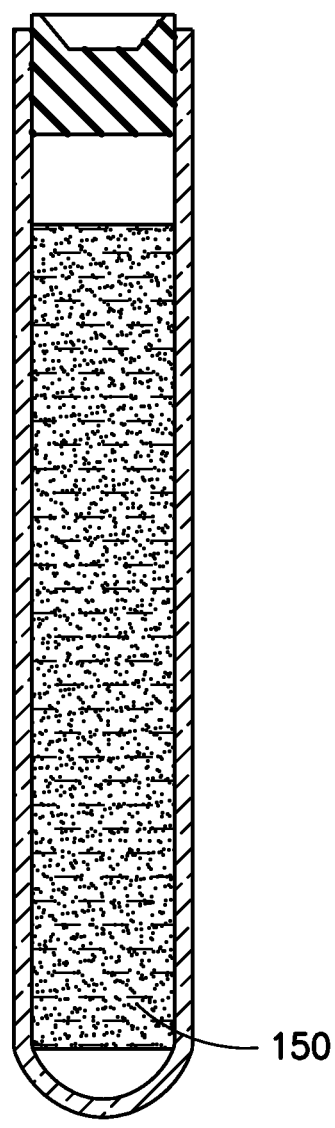
FIG. 3 illustrates the collection tube in FIG. 2 after the blood sample has undergone a cell lysing step.

Referring generally to FIGS. 1-6, a bacterial pre-concentration and detection system generally includes a collection tube 110, a sensor 120 located at the bottom of the collection tube, a moveable stopper 130 capable of being moved from a first position nearer the top of the tube and a second position nearer the bottom of the tube. The collection tube also includes a piston 300 (FIG. 5) operatively connected to a mechanism for moving the stopper 130 down the inside of the collection tube 110, and a hollow needle 400 (FIG. 5) penetrating the stopper 130 and creating fluid communication with the inside of the collection tube 110. In one embodiment, the mechanism for moving the stopper 130 up or down inside the collection tube is a robotic mechanism.

In a bacterial pre-concentration and detection technique according to one embodiment of the invention, a sample is collected from a patient into the collection tube 110 as seen in FIG. 2. The sample can include, for example, saliva, urine, blood, or other body fluids. In one embodiment of the invention, the sample is a body fluid that is normally devoid of bacteria, such as blood. When performing the bacterial pre-concentration and detection using blood, for example, a 10 mL blood sample 150 is collected into an evacuated collection tube 110 equipped with a movable stopper 130 for sealing the tube. Referring to FIG. 1, the collection tube can include a preloaded reagent mixture 160 that includes, for example, a lysing reagent such as purified Saponin (which lyses other sample constituents but not the target microorganisms, which remain viable for detection), an anti-coagulant such as polypropylene glycol, and an antifoaming reagent such as sodium polyanetholsulphonate in aqueous solution.

As seen in FIG. 2, the sample 150 is collected directly from the patient into an evacuated tube 110, such as a VACUTAINER® tube produced by Becton Dickinson and Company. For example, a traditional butterfly needle can be used with a first end located at the sample source in, the patient (e.g. in a vein) and with a second end connected to a needle 200 extending through the stopper 130 and into the evacuated collection tube 110. The collection step may alternatively include multiple steps, wherein the sample is first collected from the patient, undergoes some sort of processing, and is then fed into the collection tube.

After collecting the clinical blood sample 150, shown in FIG. 2, cells in the sample 150 other than the target microorganisms are preferably lysed. This can be accomplished, for example, by manually inverting the tube four to five times to mix the blood sample 150 with the preloaded reagent mixture 160. A goal of this step is to minimize the amount of cells, other than the target microorganisms, available in the sample 150 to aggregate and generally "clog up" the system. Depending on the source, a blood sample can have a hematocrit value around 50%. Without lysing the red blood cells ("RBCs"), a 10 mL blood sample will contain about 5 mL of RBCs. Without a lysis step, a large volume of RBCs will aggregate at the bottom of the collection tube 110 during centrifugation. This mass of RBCs has the potential to adversely affect the system operation. For example, the RBC mass can inhibit the sensor 120 function. The RBC mass can also adversely affect stopper function by preventing the stopper 130 from moving down the collection tube 110. The sample lysis described herein causes cells, other than the target microorganisms for assay, to break apart into smaller constituents and remain suspended during the centrifugation step. This reduces the likelihood of any "clogging" of the system.

Figure 4:
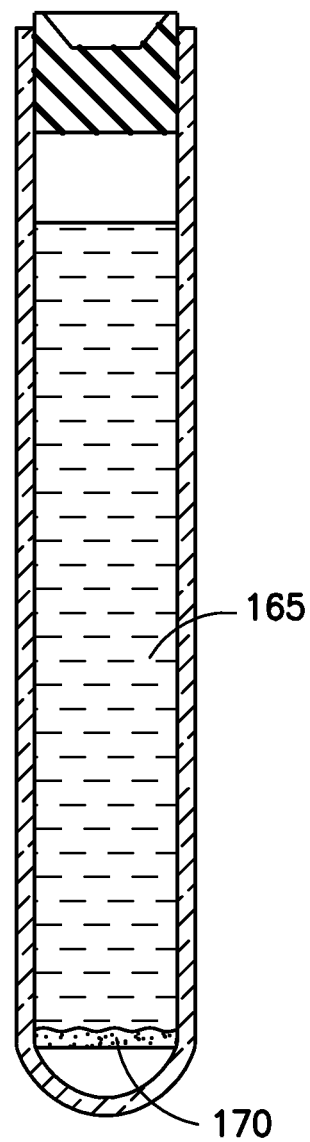
FIG. 4 illustrates the collection tube of FIG. 3 after a centrifugation step.

In the next step, shown in FIG. 3, the needle 200 is removed from the stopper 130. The stopper is preferably made of rubber or another resilient or elastomeric material such that the stopper 130 provides a seal between the stopper 130 and the inside walls of the container 110 when in contact with the inside of the collection tube 110. The stopper 130 is also preferably resilient as to provide a seal within the stopper 130 even after the needle 200 is removed. One example of such a stopper is a septum closure. Septum closures are well known to those skilled in the art and not described in detail herein. In septum closures, the hole created in the material of the stopper 130 by a needle 200 is sealed by virtue of the resilience of the stopper 130 after the needle 200 is removed. Once the needle 200 is removed, the tube 110 containing the lysed sample 150 is centrifuged to form a target pellet 170 at the tube bottom, with the remaining sample comprising supernatant 165, as best seen in FIG. 4. Efficient centrifugation can be achieved applying 3000 times gravity for approximately 30 minutes, but shorter or longer centrifugation times may be also sufficient. The centrifugation step acts to concentrate microorganisms toward the bottom of the collection tube.

Referring now to FIG. 5, following the centrifugation step, the centrifuged tube is then placed into an automated detection system (not shown) wherein a hollow needle 400 pierces the stopper and a robot-controlled piston 300 forces the movable stopper 130 toward the bottom of the collection tube 110 in the direction $D_1$. In the embodiment illustrated in FIG. 5, the piston 300 only moves the stopper 130 down in the direction of $D_1$. In other embodiments, the piston 300 is fixedly connected to the stopper 130, for example with a threaded connection, such that the piston 300 can move the stopper 130 both up and down the collection tube 110. The robotic mechanism for driving the piston is not illustrated in FIG. 5. Such mechanisms are well known to those skilled in the art and not described in detail herein.

The goal of this step is to reduce the total volume of the sample while retaining, and preserving as many of the microorganisms in the collection tube as possible. In order to reduce the volume of the sample in which the microorganisms are concentrated, an outlet path for the supernatant 165 is provided. In one embodiment, the outlet path is a hollow needle 400 that creates a path of fluid communication between the interior of the collection tube 110 and an exterior reservoir, such as a waste reservoir 500. As the piston forces the stopper 130 further into the tube 110, the increasing pressure forces the sample through the outlet path provided by the needle in the direction of $D_2$.

Moving the stopper 130 towards the tube 110 bottom causes: (i) almost all of the supernatant 165 to be forced from the tube through the hollow needle 400 fed through the stopper 130, and (ii) a very small chamber volume of approximately 200-500 μL to be formed near the tube 110 bottom that contains the target pellet 170, the sensor 120, a controlled small amount of supernatant 165, and a controlled volume of headspace gas 190 (FIGS. 7A-C). Because the earlier centrifugation step forced most or all of any existing microorganisms towards the bottom of the tube 110, and further due to the location of the hollow needle 400 near the top of the tube 110, few or no microorganisms are forced out of the tube 110 with the supernatant 165 during this volume reduction step.

Now referring to FIG. 6, once the stopper 130 has been moved into proximity with the tube 110 bottom, and most of the supernatant 165 has been ejected from the tube 110, the automated detection system begins interrogating the sensor 120 for early signs of bacterial growth. The interior of the automated detection system is temperature-controlled to provide optimum conditions for bacterial growth. In one example, the automated detection system targets about 35 degrees Celsius to support maximum bacterial growth.

Compared with a conventional blood culture bottle of approximately 90 mL overall volume, the chamber volume generated according to the process described herein is 180-450 times smaller. This means that 180-450 times fewer microorganisms are required to produce the same change in the concentration of a metabolic product of a microorganism or, in other words, for detecting a positive sample. Consequently, the technique described herein allows for shorter TTDs, even with the same sensor used in a conventional culture bottle.

Mathematical modeling of the blood culturing and detection process by the inventor has shown that a significant further shortening in the TTD can be achieved by improving the useful analyte resolution of the sensor. This can be done, e.g., by utilizing a sensor material that is exhibiting an isosbestic point. Such sensors are well known to those skilled in the art and are described in U.S. Pat. No. 5,580,784 to Berndt, which is incorporated by reference herein.

In another aspect of the invention, as seen in FIGS. 7A-C, the amount of headspace gas 190 between the top of the supernatant 165 and the bottom of the stopper 130 can be precisely controlled based on the location of the bottom of the hollow needle 400. For example, if the needle 400 extends only a short distance beyond the stopper 130, as in FIG. 7A, headspace gas 190 will initially be forced out of the collection tube 110 as the piston 300 forces the stopper 130 and needle 400 further down into the collection tube 110. Stated in another way, the height of the headspace gas 190 remaining between the top of the supernatant 165 and the bottom of the stopper 130 will be approximately equal to the distance which the needle 400 extends below the stopper 130. Based on this, the volume of headspace gas 190 remaining in the collection tube can be precisely controlled. For example, by causing the needle 400 to extend farther into the collection tube 110 (with increasing distances seen in FIGS. 7B-C), the amount of remaining headspace gas 190 will increase relative to the amount remaining when using a configuration with a shorter protrusion of needle 400 (FIG. 7A).

Controlling the headspace allows for controlling the amount of headspace gas. The desired amount of headspace gas may vary depending upon the method used to transfer sample into the collection tube. For example, when blood is drawn from a patient with a VACUTAINER® Safety Collection Device, produced by Becton Dickinson and Company, a butterfly sample collection device is used to conduct blood from the patient into the evacuated tube. The first needle of the collection device (not shown) is first inserted into a vein of the patient and, as the blood starts to flow slowly through the tubing, the second needle 200 in the collection device is inserted into the tube 110 through the stopper 130, as shown in FIG. 2. Depending on when the second needle 200 is inserted into the evacuated collection tube, 110, more or less air 190 from the tubing will enter the evacuated collection tube 110. Since this could result in variations in the headspace gas 190 volume, the disclosed control mechanism is advantageous for stabilizing the final headspace gas 190 volume. This can further be of importance because different organisms can reach optimal growth conditions in different volumes of headspace. gas. When trying to identify an unknown organism, leaving at least some headspace gas volume can be preferred, since some organisms either require or achieve improved growth in the presence of the headspace gas. The skilled person can also determine the amount of head space volume for particular organisms to achieve optimal growth conditions.

By confining the growing microorganisms within the small chamber, and by utilizing a sensor 120, the TTD obtainable according to the methods disclosed herein can be reduced to values of 50% or even greater of the TTD observed on a conventional automated detection system. The amount of reduction in TTD will depend, inter alia, on the volume reduction of the sample, with smaller volumes corresponding to shorter times. The sensor 120 can be, for example, one described in U.S. Provisional Patent Application Ser. No. 61/599,100 or a chemical sensor, such as an ion sensitive field-effect transistor or other sensor that detects a change in pH. The timing gain in hours would be most noticeable for slow growing microorganisms. The so-called Five-Day Protocol for growing such microorganisms could be shortened to a shorter time period, for example a 2.5-day protocol or even shorter.

If the detection step returns a positive result for microorganism growth, further steps such as identification (e.g. MALDI time of flight) or antibiotic susceptibility (AST) may be desirable. MALDI and AST are well known to those skilled in the art and not described in detail herein. In order to perform further tests, it may be necessary to increase the number of microorganisms in the sample. Further steps can be performed to increase the number of microorganisms to a suitable level without requiring removal of the microorganisms from their environment in the container 110, reducing the complexity of the process, the likelihood of sample contamination, and the risk of possible exposure to personnel.

Figure 8:
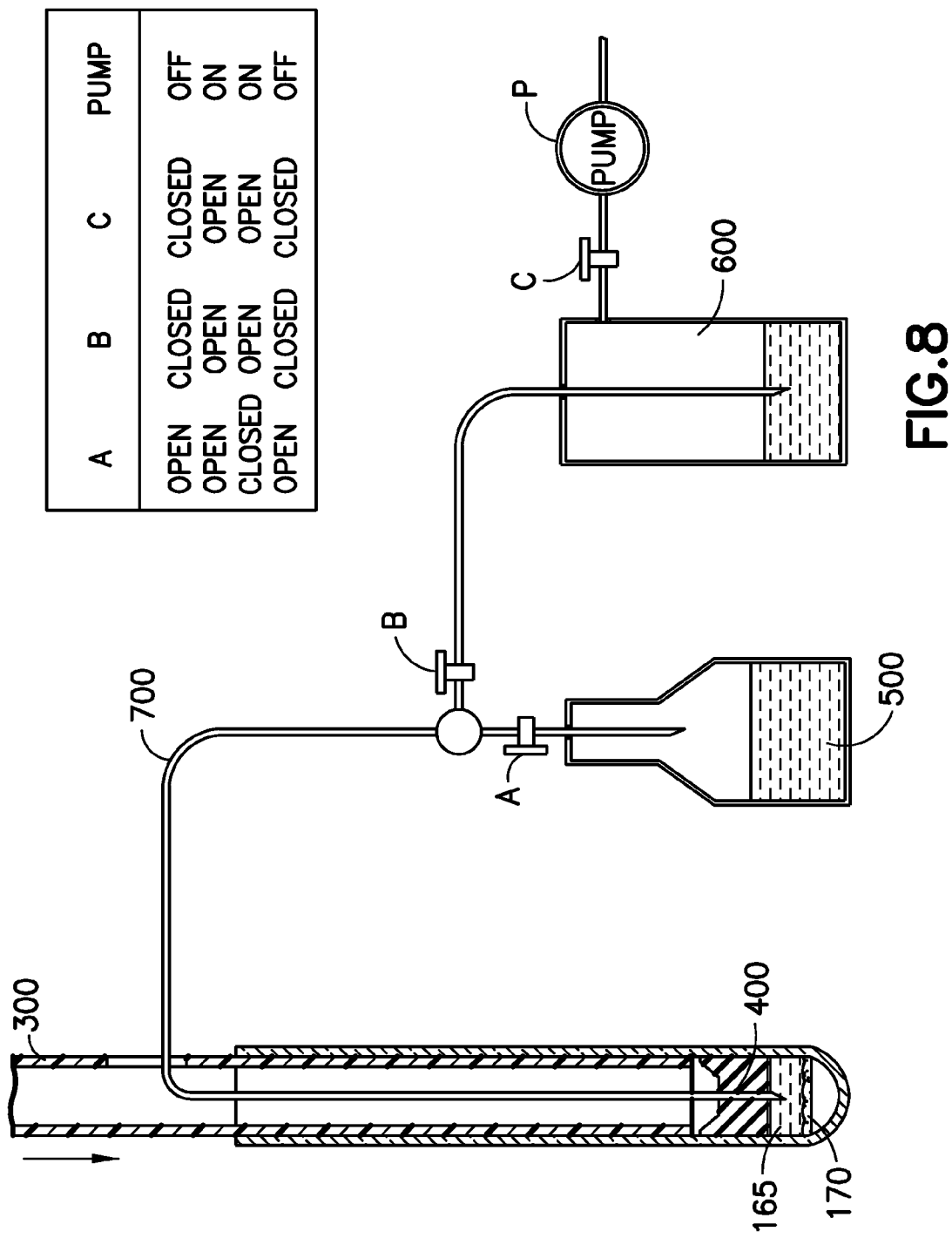
FIG. 8 illustrates a collection tube operatively coupled to waste and media reservoirs according to an embodiment of the invention.

As shown in FIG. 8, a waste reservoir 500 and nutrient reservoir 600 are each in fluid communication with the supernatant/sample 165/170 by virtue of tubing 700. The waste reservoir 500 is separated from the system by valve A. The nutrient reservoir is isolated from the system by valves B and C. The system also includes a pump P, isolated from the system by valve C.

After the collection, lysis, and centrifugation steps described with reference to FIGS. 1-4 are performed, the collection tube 110 is placed in an automatic detection system. This is similar to the step described with reference to FIGS. 5-7, although in this embodiment of the invention the collection tube 110 is connected to the system shown in FIG. 8. During a volume reduction step, the piston 300 forces the stopper 130 toward the bottom of the tube 110, forcing the supernatant 165 to escape through needle 400 and tubing 700 into waste reservoir 500. During this step, valve A is open and valves B and C are closed to isolate the media reservoir 600 and pump P from the remainder of the system.

The volume reduction and microorganism growth and detection steps proceed in a similar manner as that described with reference to FIGS. 5-6. Once detection is complete, however, it is now possible to grow any detected microorganisms into a larger number in a larger volume while maintaining the microorganisms sealed in their environment.

After the microorganisms have been positively detected, valve A is closed, and valves B and C are opened, putting the pump P, nutrient reservoir 600 and sample 165 in fluid communication. The pump P is turned on and nutrients are fed through the tubing 700 into the collection tube 110 with the microorganisms 170, causing the stopper 130 to move up the collection tube 110 as the volume of the sample 165 increases. This provides nutrients to the microorganisms 170 such that the microorganisms can grow to a sufficient number for downstream processing. If a flush of the system is desired, valves A, B and C are all opened and the pump P is turned on.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

INDUSTRIAL APPLICABILITY

The present invention can be applied to microorganism detection apparatus in which, for example, a collection tube with a moveable plunger is used to concentrate microorganisms for more rapid detection.

The invention claimed is:

1. A system for determining the presence of a microorganism in a sample by concentrating the microorganism in the sample and culturing the sample with the increased microorganism concentration, the system comprising:
a container adapted to receive a sample in a reservoir having a plunger-defined volume, the container having a first end and a second end;
a sensor inside the container near the second end configured to detect a change in the sample indicative of at least one of the presence or absence or response of a microorganism in the sample;
a retractable plunger defining within the container the plunger-defined volume of the reservoir between an end of the plunger and the second end of the container, the plunger being configured to move from the first end of the container toward the second end of the container thereby reducing the volume of the plunger-defined reservoir in which the sample is disposed, the plunger adapted to maintain a seal between the inside of the container and the outside of the container as the plunger moves from the first end of the container toward the second end of the container, the first and second ends of the container being in fluid communication with one another when the plunger is at the first end of the container;
a channel extending through the plunger configured to allow for a top portion of the sample to be forced through the channel as the plunger moves from the first end of the container toward the second end of the container, thereby reducing a volume of the sample and increasing the concentration of the microorganism in the sample remaining in the reduced volume reservoir;
a reagent mixture introduced in the container, the reagent mixture including a lysing reagent to selectively lyse cells in the sample other than the microorganism;
a waste reservoir coupled to the channel;
a nutrient reservoir coupled to the channel; and
a pump operably coupled to the nutrient reservoir, the pump configured to drive fluid flow from the nutrient reservoir into the container thereby causing the plunger-defined volume to increase by adding nutrients to the sample volume;
wherein the reagent mixture is present in the container and in fluid communication with the sensor and the sample as the plunger is advanced from the first end of the container toward the second end of the container.

2. The system of claim 1, wherein the reagent mixture further includes at least one of an anti-coagulant and an antifoaming reagent.

3. The system of claim 1, further comprising a piston in cooperating contact with the plunger wherein the piston drives the plunger to move within the container.

4. The system of claim 3, wherein the channel is at least partially disposed in the piston.

5. The system of claim 3, further comprising a needle extending through the plunger and having a first end on a first side of the plunger, a second end on a second side of the plunger, and a lumen from the first end to the second end.

6. The system of claim 5, wherein the lumen of the needle is at least a portion of the channel.

7. The system of claim 6, wherein the second end of the needle is in fluid communication with tubing, the tubing extending through at least a portion of the channel in the piston, the tubing being in fluid communication with the waste reservoir and the nutrient reservoir.

8. The system of claim 1, wherein the tubing is operatively connected to the pump.

9. The system of claim 3, configured to connect to a robotic mechanism for driving the piston.

10. The system of claim 9, wherein the piston is coupled to the plunger, the piston being capable of driving the plunger from the first end of the container toward the second end of the container and from the second end of the container toward the first end of the container.

11. The system of claim 10, wherein the piston is threaded onto the plunger and the plunger is configured to receive the threaded portion.

12. The system of claim 1, wherein movement of the plunger from the first end of the container toward the second end of the container is configured to drive the top portion of the sample into the waste reservoir, and the plunger is configured to move from the second end of the container toward the first end of the container coincident with fluid flow from the nutrient reservoir into the container.

13. The system of claim 3, wherein the piston is configured to move the plunger from the second end of the container toward the first end of the container to cause fluid flow from the nutrient reservoir into the container.

* * * * *